(12) United States Patent
Kumar et al.

(10) Patent No.: US 7,749,369 B2
(45) Date of Patent: Jul. 6, 2010

(54) GEL PROCESSING AND TRANSFER DEVICE

(76) Inventors: Sanjay Kumar, Institute of Himalayan Bioresource Technology, Himachal Pradesh, Palampur 176 061 (IN); Dhiraj Vyas, Institute of Himalayan Bioresource Technology, Himachal Pradesh, Palampur 176 061 (IN)

( * ) Notice: Subject to any disclaimer, the term of this patent is extended or adjusted under 35 U.S.C. 154(b) by 1108 days.

(21) Appl. No.: 11/265,883

(22) Filed: Feb. 17, 2006

(65) Prior Publication Data
US 2006/0257291 A1  Nov. 16, 2006

Related U.S. Application Data

(63) Continuation of application No. 09/803,645, filed on Mar. 9, 2001, now abandoned.

(51) Int. Cl.
*G01N 27/447* (2006.01)
*G01N 33/559* (2006.01)

(52) U.S. Cl. .................. 204/615; 204/465; 204/466; 204/606; 204/613; 204/614; 435/288.3

(58) Field of Classification Search ......... 204/462–466, 204/606, 613–615; 435/288.3
See application file for complete search history.

(56) References Cited

U.S. PATENT DOCUMENTS

| | | | | |
|---|---|---|---|---|
| 3,875,045 A | * | 4/1975 | Bergrahm et al. | 422/82.01 |
| 4,020,563 A | * | 5/1977 | Hoefer | 34/552 |
| 4,142,960 A | * | 3/1979 | Hahn et al. | 204/619 |
| 4,234,400 A | * | 11/1980 | Kaplan et al. | 204/461 |
| 4,314,897 A | * | 2/1982 | Monte et al. | 206/449 |
| 4,576,693 A | * | 3/1986 | Kreisher et al. | 264/219 |
| 4,756,809 A | * | 7/1988 | Love et al. | 204/464 |
| 4,759,838 A | * | 7/1988 | Mayes et al. | 206/449 |
| 4,773,984 A | * | 9/1988 | Flesher et al. | 204/618 |
| 4,877,510 A | * | 10/1989 | Chen | 204/613 |
| 4,913,791 A | * | 4/1990 | Hurd et al. | 204/614 |
| 4,957,613 A | * | 9/1990 | Schuette | 204/618 |
| 5,112,470 A | * | 5/1992 | Sylvester | 204/618 |
| 5,137,613 A | * | 8/1992 | Brumley et al. | 204/620 |
| 5,155,049 A | * | 10/1992 | Kauvar et al. | 436/177 |
| 5,217,592 A | * | 6/1993 | Jones | 204/614 |
| 5,399,255 A | * | 3/1995 | Sarrine | 204/616 |
| 5,449,446 A | * | 9/1995 | Verma et al. | 204/612 |
| 5,487,822 A | * | 1/1996 | Demaray et al. | 204/298.09 |
| 5,572,802 A | * | 11/1996 | Alpenfels et al. | 34/192 |

(Continued)

FOREIGN PATENT DOCUMENTS

EP    0492769 A2 *  7/1992

(Continued)

*Primary Examiner*—Arlen Soderquist
(74) *Attorney, Agent, or Firm*—Brooks, Cameron & Huebsch, PLLC

(57) ABSTRACT

The present invention relates to a gel processing and transfer device, useful for the processing and transferring un-damaged and intact gel with minimal handling, said device comprising at least 4 separable components namely: a base plate for holding the gels with facility to drain out solution; a retaining rim with attached side-walls, said side walls are fastened to the base plate by a fastening means; at least one "O" ring fixed to the retaining rim to give leakproof arrangement with the base plate; and a lid to cover the assembly.

28 Claims, 9 Drawing Sheets

U.S. PATENT DOCUMENTS

Figure 1:
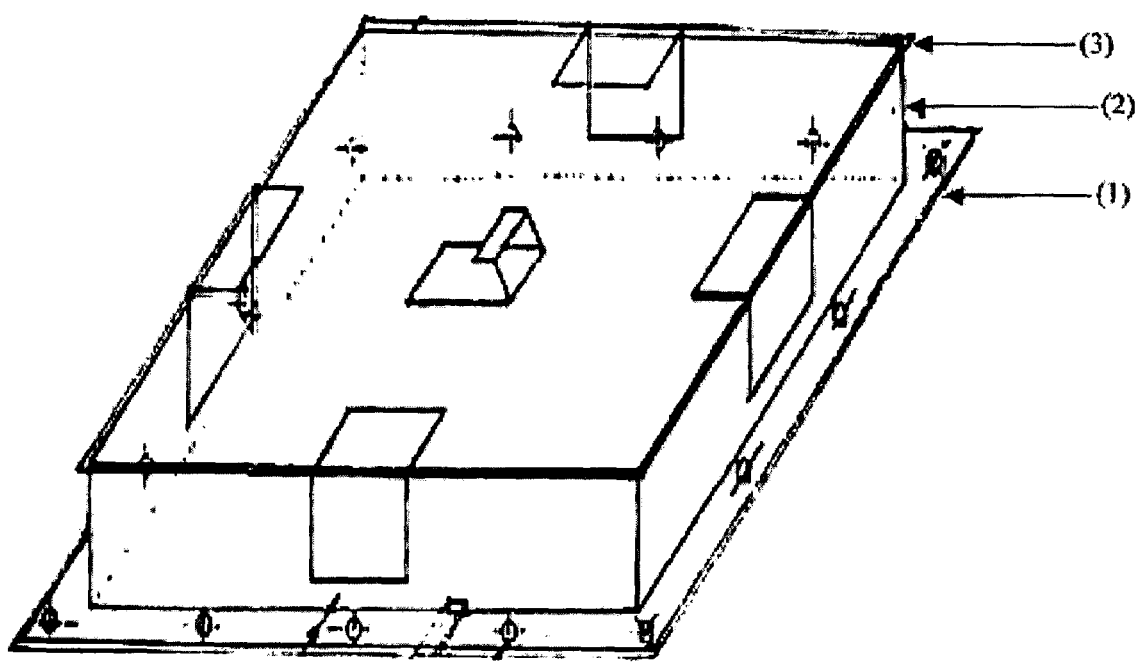

| | | | | |
|---|---|---|---|---|
| 5,626,735 A | * | 5/1997 | Chu | 204/606 |
| 5,885,431 A | * | 3/1999 | Renfrew et al. | 204/466 |
| 6,163,977 A | * | 12/2000 | Gaffar | 34/143 |
| 6,194,160 B1 | * | 2/2001 | Levin | 435/7.1 |
| 2002/0127148 A1 | * | 9/2002 | Kumar et al. | 422/102 |

FOREIGN PATENT DOCUMENTS

| | | | |
|---|---|---|---|
| WO | WO 02071049 A1 | * | 9/2002 |

* cited by examiner

GEL PROCESSING AND TRANSFER DEVICE

CROSS REFERENCE TO RELATED APPLICATIONS

This application is a Continuation of U.S. application Ser. No. 09/803,645 filed Mar. 9, 2001, now abandoned the specification of which is incorporated herein by reference.

FIELD OF INVENTION

The present invention relates to a gel processing and transfer device. The device ensures un-damaged, intact gel while performing all the steps with agarose gel or the like that are involved after electrophoresis of nucleic acids or the like and before placing the gel onto the membrane for the purpose of transfer of nucleic acids or the like. Importantly, apparatus ensures undamaged, intact gel during transfer and transportation of the gel from the device onto the membrane or like. The present invention also describes the method to use the apparatus.

BACKGROUND AND PRIOR ART REFERENCES

One of the ways to separate macromolecules such as proteins, nucleic acids, charged sugars and peptides etc. is through electrophoresis wherein, electrical voltage is applied to the moities to be separated and these move with different velocities in a solution depending upon their charge, size, shape and viscosity of the medium. To disallow diffusion of the macromolecules in solution due to convection currents, the solution is supported on a porous matrix.

A number of such matrices are available (Davis, M. G. 1986. Electrophoretic techniques. In A biologists guide to principles and techniques of practical biochemistry. (Wilson, K. and Goulding, K. H., eds.) $3^{rd}$ Ed. English Language Book Society/Edward Arnold. London. pp. 245-268; Plummer, D. T. 1988. An introduction to practical biochemistry. $3^{rd}$ Ed. Tata McGraw-Hill Publishing Company Limited, New Delhi, 332p). These include (a) paper, (b) cellulose acetate strip, (c) cellulose, silica, kieselguhr or alumina layered on a glass plate, and (d) various types of gel matrices. Gel as a supporting medium is a medium of choice in protein and nucleic acid research. This includes gels made from (a) starch, (b) agar (a mixture of agarose and agaropectin; dissolved by heating in a buffer medium to get the porous matrix), (c) agarose (a polymer of D-galactose and 3,6-anhydro L-galactose; dissolved by heating in a buffer medium to get the porous matrix), and (d) polyacrylamide.

Normally, agarose gel is a matrix of choice while working with nucleic acids. One of the requirements of working with nucleic acid is to transfer the separated nucleic acid from the gel matrix onto a membrane in a blotter. The blotter is an apparatus wherein the nucleic acids or the like are transferred from the gel onto the membrane. In a vacuum blotter, the process of transfer is assisted with the help of vacuum. This constitutes one of the most important steps of southern or northern blotting.

In southern blotting, deoxyribonucleic acid (hereinafter known as DNA) is digested with endonucleases followed by electrophoretic separation of the digested fragments on agarose gel and finally transfer of the digested DNA onto a membrane. To ease transfer of large-sized DNA from the gel onto the membrane, DNA strands need to be (i) cleaved using 0.25 M hydrochloric acid, (ii) denatured using 1.5 N sodium chloride/0.5 N sodium hydroxide to obtain single strand, and (iii) neutralized using 1.5 N sodium chloride/0.5 N tris-chloride (pH, 7.0) to allow proper binding of DNA onto the membrane onto which the transfer has to take place. After achieving these steps of processing, the gel needs to be placed onto a membrane to allow transfer of DNA from the gel onto the membrane (Ausubel, F. M., Brent, R., Kingston, R. E., Moore, D. D., Seidman, J. G., Smith, J. A. and Struhl, K. 1998. Current protocols in molecular biology. John Wiley & Sons, Inc. New York, pp. 2.8.1-2.9.15).

In northern blotting, ribonucleic acid (hereinafter known as RNA) is run on agarose gel that usually contains formaldehyde. For efficient transfer of RNA from the gel onto the membrane, RNA containing gel needs to be (i) washed several times with water, (ii) denatured using 1.5 N sodium chloride/0.05 N sodium hydroxide, (iii) neutralized using 1.5 N sodium chloride/0.5 N tris-chloride (pH, 7.4), (iv) soaked in 20×SSC (3 M sodium chloride, 0.3 M sodium citrate; adjust pH to 7.0 with 1 M hydrochloric acid). After achieving these steps of processing, the gel needs to be placed onto a membrane to allow transfer of RNA from the gel onto the membrane (Ausubel, F. M., Brent, R., Kingston, R. E., Moore, D. D., Seidman, J. G., Smith, J. A. and Struhl, K. 1998. Current protocols in molecular biology. John Wiley & Sons, Inc. New York, pp. 4.9.1-4.9.16).

These processes are normally carried out in containers which are normally baking dish or in plastic box (Sambrook, J., Fritsch, E. F. and Maniatis T. 1989. Molecular cloning: A laboratory manual. $2^{nd}$ Ed. Cold Spring Harbour Laboratory Press. New York; Ausubel, F. M., Brent, R., Kingston, R. E., Moore, D. D., Seidman, J. G., Smith, J. A. and Struhl, K. 1998. Current protocols in molecular biology. John Wiley & Sons, Inc. New York). While changing various solutions as mentioned in the above paragraph, the container is tilted to remove the solution. The gel needs to be held by hand to avoid falling of the gel along with the solution. Secondly, after giving various washes with different solutions as mentioned in the above paragraph, the gel has to taken out from the container to be placed over the membrane. This second process leads to the damage of the delicate gel. Also, the gel has to be placed onto the membrane properly and once kept onto the membrane, the gel can not be moved.

As recognized herein, the agarose gel holding precious samples of DNA or RNA is delicate and fragile, and liable to damage during various steps mentioned above. The risk of damage increases with increase in the size of the gel. Particularly, during the processing of large number of samples, the size of the gel may be as big as, but not limited to, measuring 15×22 centimeter (width×length).

This dictates the development of a gel processing and transfer device that ensures intact gel during various processes as described above.

Also, while working with proteins, the staining of the proteins requires several solutions to be changed one after another and once the proteins are stained, the photography of the gel is essential to record the data (Hames, B. D. 1990. One dimensional polyacrylamide gel electrophoresis. In Gel electrophoresis of proteins: A practical approach. (Hames, B. D. and Rickwood, D., eds.) $2^{nd}$ Ed. IRL Press at Oxford University Press, Oxford. pp. 1-147). This also dictates the development of such device, wherein intactness of the gel should be ensured during staining protocols and the device should be capable of presenting the gel for the purpose of photography.

Such a device could not be found with various firms dealing with laboratory products. The catalogue of the following firms were scanned:

(a) Fisher Scientific, 585 Alpha Dr., Pittsburgh, Pa., 15205-9913, USA.

(b) Cole-Parmer, Instrument company, 625 East Bunker Court, Vernon Hills, Ill. 60061-1844. USA.
(c) Becton Dickinson Labware, Two Oak Park, Bedford, Mass. 01730-9902, USA.
(d) Amersham Pharmacia Biotech UK Ltd., Amersham Place, Little Chalfont, Buckinghamshire, HP7 9NA, England.
(e) Brand GMBH+CO KG, Laboratory Equipment Manufactures, P. O. Box 1155 D-97861 Wertheim Germany.
(f) Sigma Chemical Co. P. O. Box 14508 St. Louis, Mo. 63178 USA.
(g) Gibco BRL Life Technologies 9880 Medical Centre Drive P. O. Box 6482 Rockville, Md. 20849-648.
(h) Consort Ltd. Parklaan 36 B-2300 Turnhout, Belgium.
(i) Bio-Rad Laboratories 2000 Alfred Nobel Drive, Hercules, Calif. 94547.
(j) S. D. Fine-Chem Ltd. 315-317, T.V. Industrial Estate, 248 Worli Road, Mumbai 400025 India.
(k) Tarsons Products Pvt. Ltd. 856 Marshell House, 33/1 Netaji Subash Road, Calcutta 700001 India.
(l) Imperial Bio-Medics, Show Room No. 36, Sector-26, Madhya Marg, Chandigarh 160019 India.
(m) Bangalore Genei Pvt. Ltd., No. 6, 6th Main, BDA Industrial Suburb, Near SRS Road, Peenya, Bangalore 560058 India.

Product number Z 35,829-0 and Z 35,830-4 by M/s Sigma Chemical Co, USA and product number 482030 by M/s Tarsons Products Pvt. Ltd., India describe a gel staining tray. However, the product is basically a plastic box structure with an outlet at the base and has the following shortcomings:

1. The product can accommodate a limited-sized gel
2. The gel is broken during transfer from the product onto a blotter Since the Product number Z 35,829-0 and Z 35,830-4 by M/s Sigma Chemical Co, USA is also similar to the one by M/s. Tarsons Products Pvt. Ltd., India (product number 482030) apart from the size, end result is likely to be the same.)

Thus, there is no gel processing and transfer device that ensures intact gel (i) during various processes that are involved after electrophoresis of nucleic acids and before placing the gel onto the membrane for the purpose of transfer of nucleic acid, and (ii) during transfer of the gel from the device onto the membrane. The patent search has been conducted to survey the existing patents relating to the use of processing and transfer of gels. The critical study of the prior patents indicates that none of them is, somehow, not at all connected to the type of applications the present invention is intended to. A new device which is being planned to be launched by the applicant would be a service through which users would be accessed to a device which will help processing and transfer of gels with minimal handling. This object of invention would be the first of its kind.

OBJECTS OF THE INVENTION

The main objects of the present invention is to provide a gel processing and transferring device.

Another object of the present invention is to provide a gel processing device which requires least handling.

SUMMARY OF INVENTION

The present invention relates to a gel processing and transferring device useful for the processing and transferring of gels with minimal handling.

BRIEF DESCRIPTION OF THE ACCOMPANYING DRAWINGS

Figure 2:
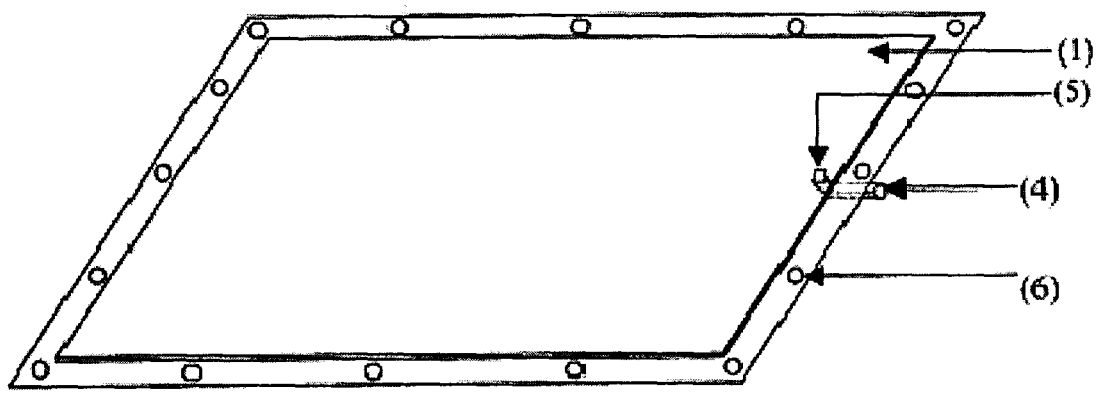
Figure 3:
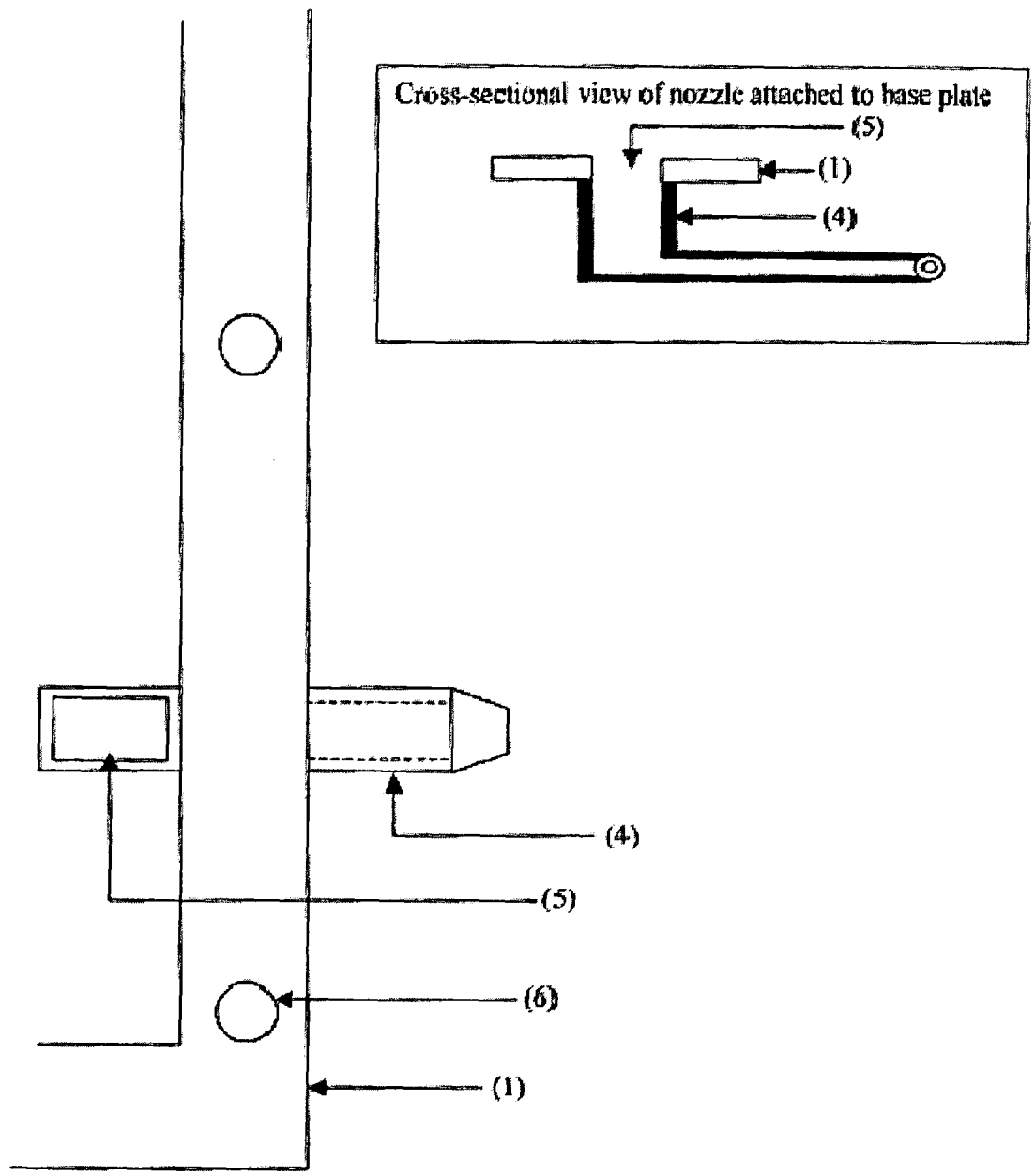
Figure 4:
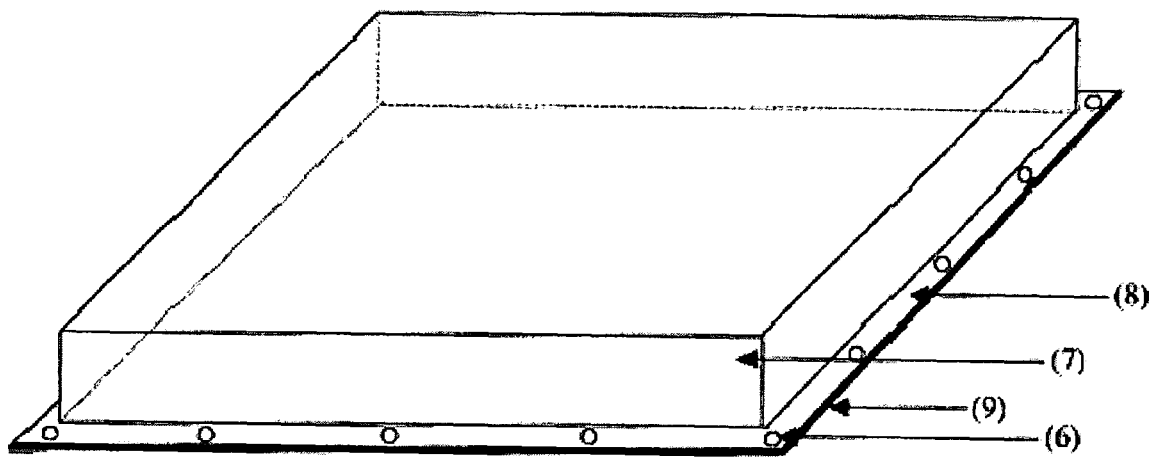
Figure 5:
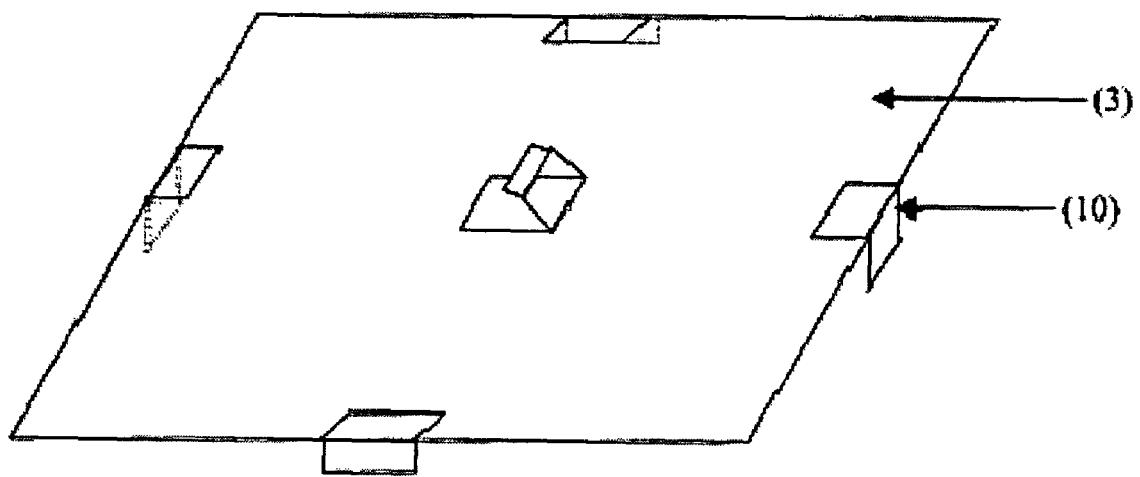
Figure 6:
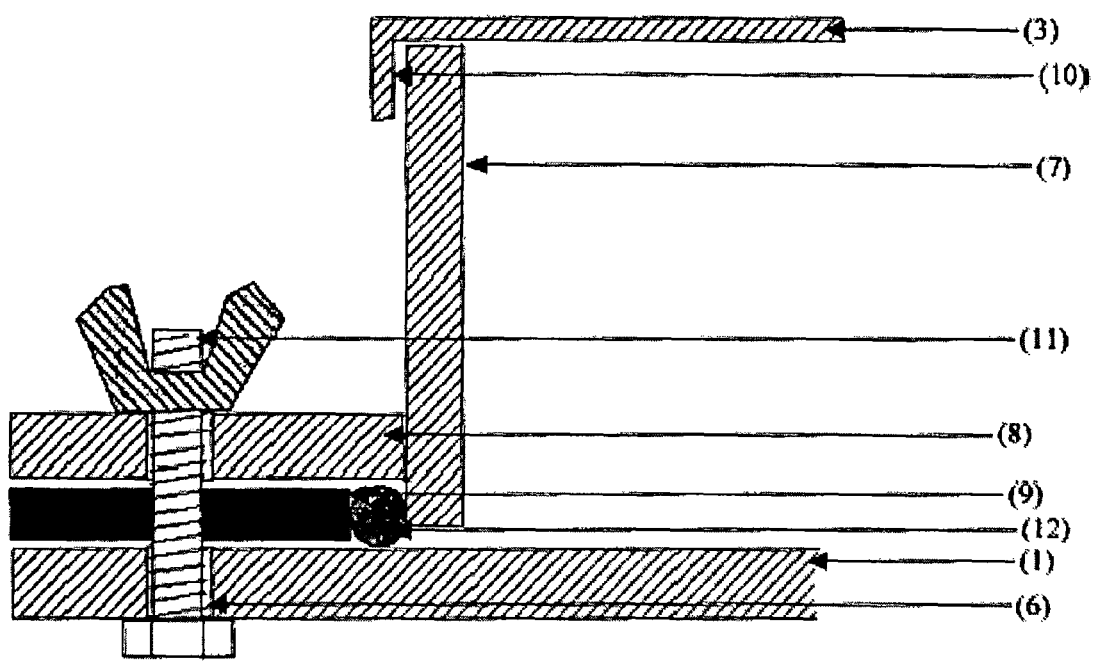
Figure 7:
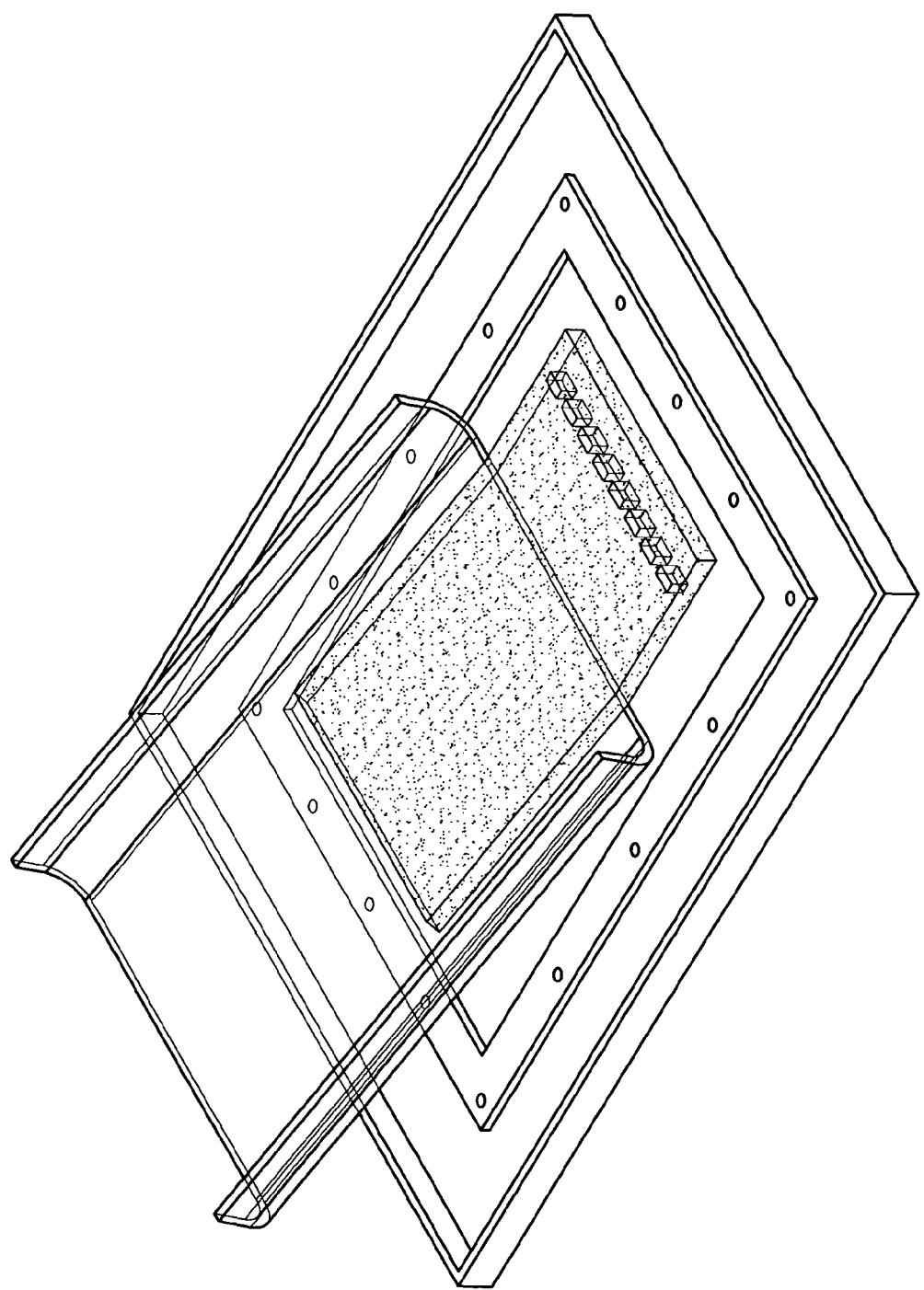
Figure 8:
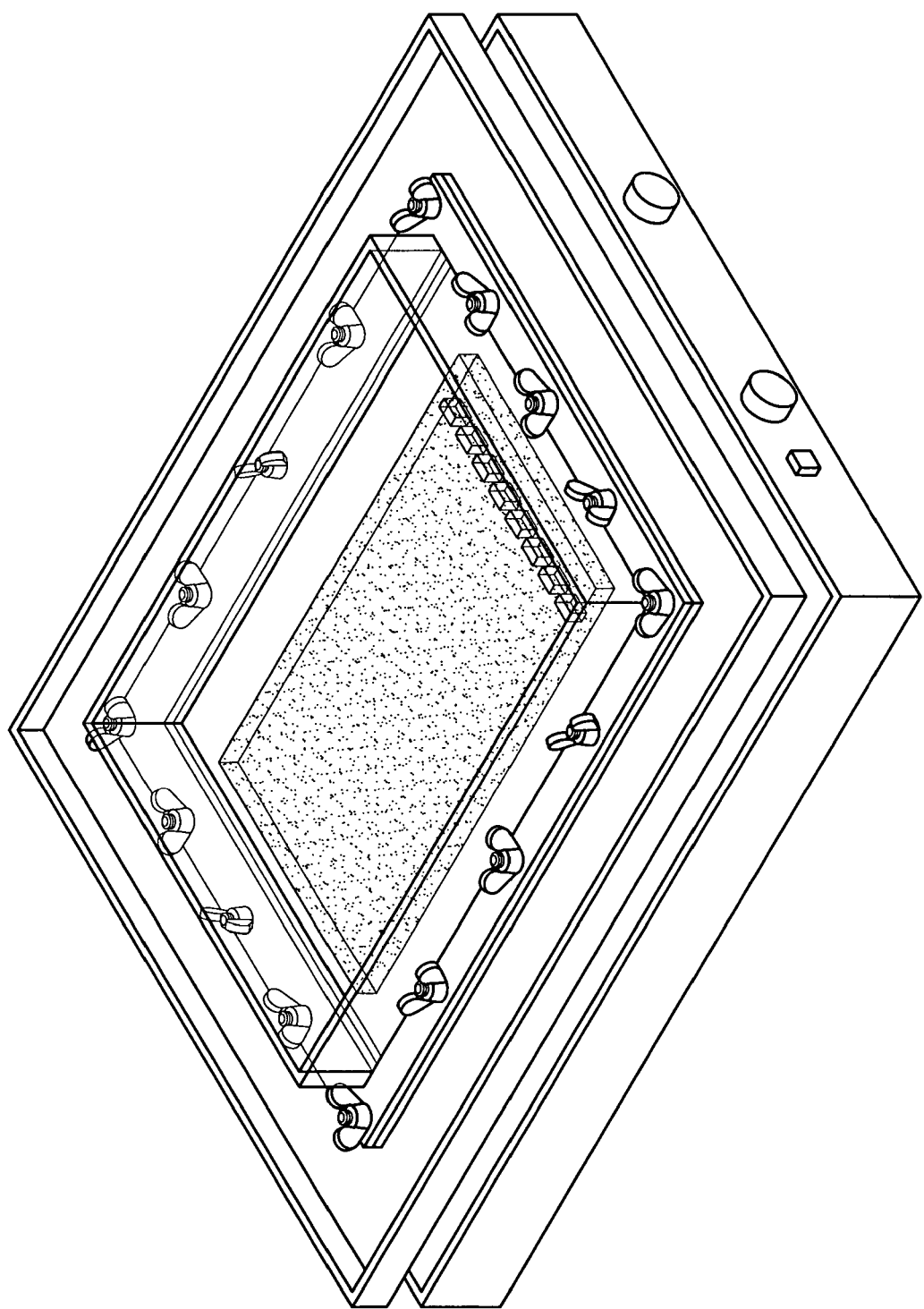
Figure 9:
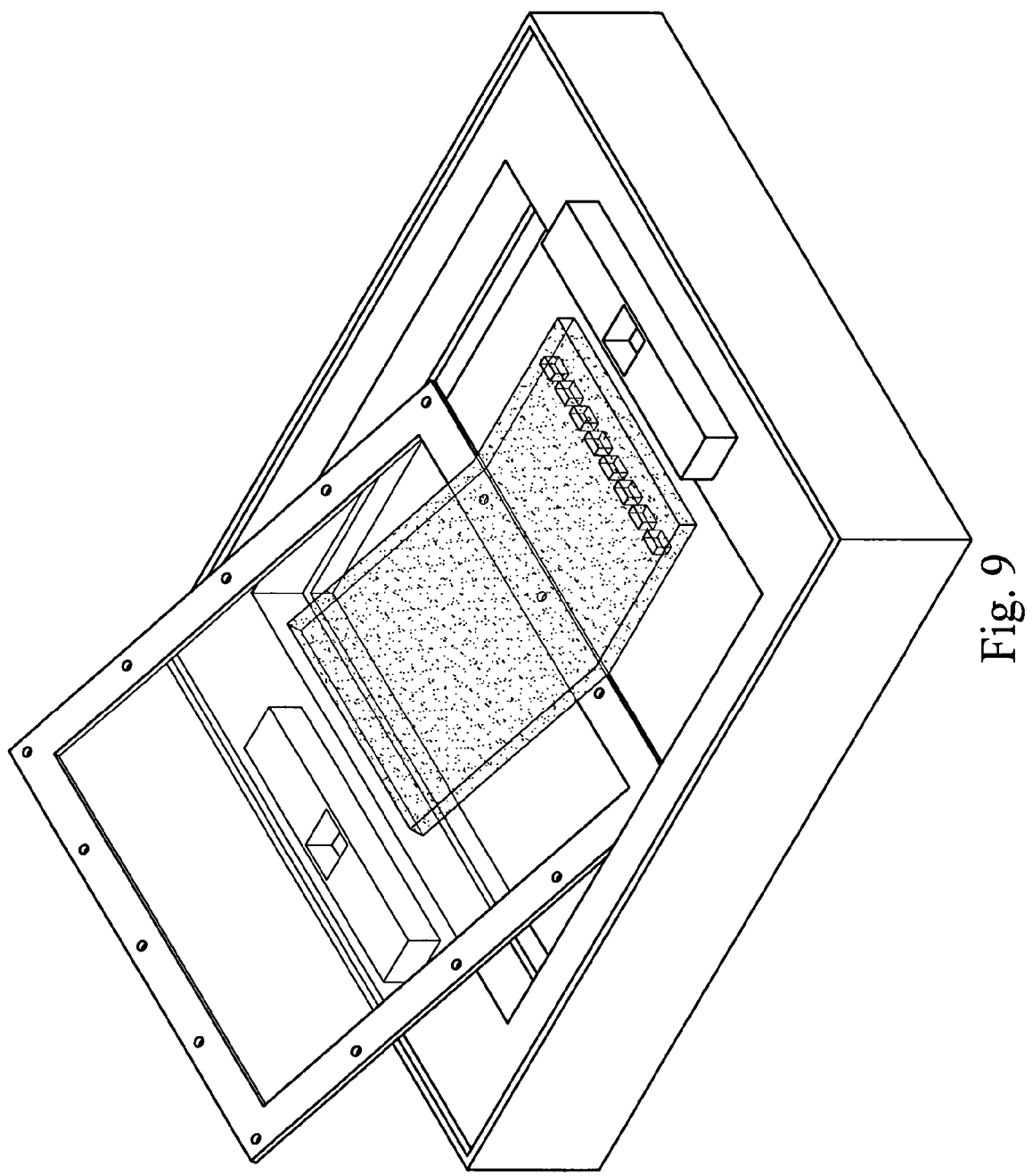

In the drawings accompanying the specification,
FIG. 1 represents an overall view of the gel processing and transfer device.
FIG. 2 represents the base plate, one embodiment of the device, which has a drain-out facility for solution.
FIG. 3 represents the drain-out facility for solution in the base plate, another embodiment of the device.
FIG. 4 represents the retaining rim, an preferred embodiment of the apparatus of invention.
FIG. 5 represents the lid, yet another embodiment of the apparatus of invention
FIG. 6 represents the cross-section of the device showing arrangement of various components.
FIG. 7 represents the transfer of gel from the electrophoresis tray onto base plate of the device.
FIG. 8 represents the processing of the gel in the invented device. The covering lid is not shown in the photograph.
FIG. 9 represents transfer of the gel from base plate of the device to a vacuum blotter.

DETAILED DESCRIPTION OF THE INVENTION

Accordingly, the invention presents a gel processing and transfer device, useful for the processing and transferring of the gels with minimal handling, comprising of at least four separable components namely, (i) a base plate for holding the gels with the facility to drain out solution, (ii) a retaining rim with attached side-walls, said side walls are fastened to the base plate by a fastening means, (iii) at least one "O" ring fixed to the retaining rim to give leakproof arrangement, and (iv) a lid to cover the assembly.

In an embodiment of the present invention, the dimension of the base plate used depends upon the size of the gel to be transferred from the electrophoresis tray to the base plate.

In another embodiment of the present invention, the base plate used is made up of materials selected from the group comprising of, polycarbonate, acrylic, plexiglas, glass, plastic, polyethylene, polypropylene, polyester, polymethacrylate, poly(1,4-cyclohexylene dimethylene terephthalate)glycol and metals.

In still another embodiment of the present invention, the base plate has a thickness of at least 1 mm.

In yet another embodiment of the present invention, one of the ends of the base plate can optionally be shaped in the form of wedge to ease transfer of the gel from the base plate onto the membrane.

In one more embodiment of the present invention, the base plate has a drain-out device to decant the poured solution.

In one another embodiment of the present invention, the drain-out device has a hole cut in center on one side of the base plate.

In an embodiment of the present invention, the hole of the drain-out device has a nozzle attached cut to fit the size of the object of invention.

In another embodiment of the present invention, the nozzle on drain-out device is made up of materials selected from the group comprising of, polycarbonate, acrylic, plexiglas, glass, plastic, polyethylene, polypropylene, polyester, polymethacrylate, poly(1,4-cyclohexylene dimethylene terephthalate)glycol and metals.

In still another embodiment of the present invention, the nozzle on the drain-out device has a tubing attached to it.

In one more embodiment of the present invention, the tube is made up of materials selected from the group comprising of, rubber, latex rubber, silicone, platinum-cured silicone (for high purity and no peroxides), C-Flex (an opaque white thermoplastic elastomer formulated from styrene-ethylene-butadiene-styrene block co-polymer, low density polyethylene, fluorinated ethylene-propylene, teflon polytetrafluoroethylene and silicone.

In one another embodiment of the present invention, the tube may be of any convenient length with inner diameter that fits exactly to the open end of the nozzle and fixed with a clamp to control the flow of the solution.

In an embodiment of the present invention, the base plate can have any type of the drain out facility to decant the poured solution.

In still another embodiment of the present invention, the retaining rim has dimension depending upon the size of the gel used.

In yet another embodiment of the present invention, the retaining rim is made up materials selected from the group consisting of, polycarbonate, acrylic, plexiglas, glass, plastic, polyethylene, polypropylene, polyester, polymethacrylate, poly(1,4-cyclohexylene dimethylene terephthalate)glycol and metals.

In one more embodiment of the present invention, the retaining rim has a thickness of at least 1 mm.

In one another embodiment of the present invention, the retaining rim has sidewalls of height of at least 1 cm.

In an embodiment of the present invention, the sidewalls of the retaining rim are attached perpendicular to horizontal plates and 2 cm wide from the horizontal plates to ensure that the horizontal plates are always outside the sidewalls.

In another embodiment of the present invention, the sidewalls of the retaining rim are attached with the horizontal plate in a way so that 2 mm of side-walls always protrude below the horizontal plate.

In still another embodiment of the present invention, the base plate and retaining rim are fastened together by any of the conventional methods.

In yet another embodiment of the present invention, the fastening mechanism are selected from the group comprising of nut and bolts, clamps, bolts with plastic fitted caps and nuts engraved in the base plate.

In one more embodiment of the present invention, the fastening mechanism as used, is selected from the material comprising of the group acrylic, plexiglas, glass, plastic, polyethylene, polypropylene, polyester, polymethacrylate, poly(1,4-cyclohexylenedimethyleneterephthalate) glycol and metals.

In one another embodiment of the present invention, the retaining rim used has at least one "O" ring to avoid leakage of solution from the assembly of base plate and retaining rim.

In an embodiment of the present invention, the "O" ring is made up of materials selected from the group comprising of rubber, latex rubber, silicone, platinum-cured silicone (for high purity and no peroxides), C-Flex (an opaque white thermoplastic elastomer formulated from styrene-ethylene-butadiene-styrene block co-polymer), low density polyethylene, fluorinated ethylene-propylene, teflon polytetrafluoroethylene and silicone.

In another embodiment of the present invention, the "O" ring used is fitted around the protruded portion of the sidewalls of the retaining rim.

In still another embodiment of the present invention, the "O" ring used can optionally be placed inside the grove of the base plate.

In yet another embodiment of the present invention, the lid used depends upon the size of the assembly made by the sidewalls of the retaining rim.

In one more embodiment of the present invention, the lid used is made up of the materials selected from the group comprising of polycarbonate, acrylic, plexiglas, glass, plastic, polyethylene, polypropylene, polyester, polymethacrylate, poly(1,4-cyclohexylene dimethylene terephthalate)glycol and metals.

In one another embodiment of the present invention, the lid used has a thickness of at least 1 mm.

In an embodiment of the present invention, the lid rests on the top of sidewalls of the retaining rim and can be easily covered and removed.

In another embodiment of the present invention, the lid as used has at least four protrusions attached onto the top, that keep the lid fixed, onto the sidewalls of the retaining rim from outside and the dimension of which depend upon the height of the side walls of the retaining rim.

In still another embodiment of the present invention, the protrusions in the lid as used, is selected from the material, from the group consisting of, polycarbonate, acrylic, plexiglas, glass, plastic, polyethylene, polypropylene, polyester, polymethacrylate, poly(1,4-cyclohexylene dimethylene terephthalate)glycol or metal of choice, but is not limited to the said group.

In yet another embodiment of the present invention, the protrusions on the lid, has a thickness of at least 1 mm.

In one more embodiment of the present invention, if various parts are moulded, a better finished and more durable product will be produced.

In one another embodiment of the present invention, the whole unit or individual components, could be a part of the automation unit leading to robotic-gel-transfer.

In an embodiment of the present invention, the said device ensures intact gel during different processes involved after electrophoresis and during transportation.

In another embodiment of the present invention, the device constructed with autoclavable material ensures sterile environment to the gel.

In still another embodiment of the present invention, the device constructed with metal with no heat-sensitive component has uses in food industry particularly will be useful to bake cake, bread and/or the like with no damage to the product.

In yet another embodiment of the present invention, the device is used in giving desired shape to the jelly and/or the like material.

In one more embodiment of the present invention, the device is transparent to various lights, translucent, opaque, impermeable to light or the like material.

The following example is given by the way of illustration of the device of the present invention and it should not be construed to limit the scope of the present invention.

Example 1

General Method for Construction of the Device

The present invention provides with an apparatus, a gel processing and transfer device, that consists of at least four separable components. In FIG. 2 of the drawings accompanying this specification, the base plate of the device of present invention is depicted. The base plate (1) of the device has a nozzle (2) attached to the rectangular hole (3). A silicone tubing (4) along with a clamp (5) is fixed onto the open end of the nozzle. In FIG. 6. of the drawings accompanying this specification, an arrangement of the various components of the device is shown. Retaining rim (6) of the device is attached to the base plate using nuts and bolts (7). Holes (8)

are drilled on the outer edge of the base plate and the retaining rim for fastening nuts and bolts. The retaining rim has four side walls (9) joined perpendicularly to the horizontal plate (10) in such a way that side walls protrude below the horizontal plate. A rubber strip (11) is fixed outside the protrusion on the lower side of the horizontal plate. An "O" ring (12) is placed in the room created by the protrusion of the side walls and the horizontal plate of the retaining rim.

After fastening the base plate and the retaining rim, lid (13) is placed over the side walls of the retaining rim. The lid remains fixed onto the assembly with the help of at least four protrusions (14) attached to the lid.

Example 2

Preparation of the Base Plate

The base plate was prepared using a 2 mm thick polycarbonate sheet, cut with the help of hexagonal blade exactly measuring to size of 28×22 cm. To give strength to the edges a 2 cm wide and 2 mm thick polycarbonate sheet is glued using chloroform (organic solvent), to the base plate. A drain out facility is made in the base plate by making a 0.5×0.5 cm hole on 28 cm long side of the base plate at a distance of 11 cm from one end of the length. Width-wise, the hole is placed at a distance of 19.5 cm from one end of the 22 cm wide base plate. To the hole a small nozzle measuring 4.5 cm is attached. The nozzle is prepared with the pieces of 2 mm thick polycarbonate sheet, cut to fit the size. To the nozzle a silicone tube, 30 cm in length, exactly fitting to the open end of the nozzle (with inner diameter of 0.6 cm), is attached. A clamp is placed onto the silicone tube to control the flow of solution.

To fasten the base plate, to the retaining rim; holes (diameter 1 cm) are drilled on the base plate, at a distance of 1 cm from the outer edge in both the directions. A total of 5 holes are drilled on the side measuring 28 cm and a total of 4 holes are drilled on the side measuring 22 cm. The holes at the corners are common on length and width-wise.

Example 3

Preparation of the Retaining Rim

The retaining rim of the object of invention is prepared using 2 mm thick polycarbonate sheet measuring 28×22 cm in outer dimension. The inner plate of 24×18 cm was cut and removed from the overall plate to give a gasket of polycarbonate. A similar gasket was cut from a different plate and glued onto the first to give additional strength to the retaining rim. The side walls of retaining rim are made from a single 84 cm long and 4 cm wide piece of 2 mm thick polycarbonate, bent at 3 corners at an angle of 90° to obtain a rectangular structure. The side walls of retaining rim thus formed brings two free ends of the polycarbonate piece together to allow joining. The side-walls of retaining rim is attached perpendicularly to 2 cm wide horizontal plates in such a way that the horizontal plates are always outside the retaining rim. Attachment of side-walls of retaining rim with the horizontal plate, is performed in such a way that 2 mm of side-walls always protrude below the horizontal plate. This arrangement gives an effective height of 4.2 cm to the retaining rim.

After fastening the nuts and bolts to the retaining rim and the base plate, the assembly looks like an open rectangular box that forms an enclosure offering an effective space of 24×18 cm onto the base plate.

Example 4

Preparation of No-Solution-Leak System

To check the leakage from the apparatus a rubber "O" ring (4 millimeters thickness) is placed under the retaining rim. The "O" ring is placed in the space provided by the protrusion of side walls to the horizontal plates of the retaining rim. Since the horizontal plate of the side rim actually sits on the base plate, the placing of an "O" ring on the retaining rim creates a gap, which may lead to damage of horizontal plates during fastening with nut and bolts. To avoid this, a rubber strip of 1.5 mm thickness was fixed around the "O" ring on the retaining rim. Such an arrangement resulted into a "no-solution-leak" system.

Example 5

Preparation of the Lid

The lid is an important component of the object of invention and provides safety to the gel and to the solution in the object of invention. Also, it will check evaporation of solutions from the device The lid measuring 24×18 cm is constructed using a 2 mm thick polycarbonate sheet. To avoid slipping of the lid from top of the retaining rim, a 2.5 cm long and 4.0 cm wide protrusion made with polycarbonate is fixed onto the top of the lid. The protrusion covers the retaining rim from out-side and fixes the lid on to the side walls of the retaining rim in the complete assembly. A folded piece of polycarbonate was fixed in the center of the lid to give a handle for lid and eases its movement.

Example 6

Method to Use the Device

The invention describes the method to use the device for the agarose gel or the like containing nucleic acids or the like. The following sequence should be followed:
(i) Autoclave the complete assembly of the object of invention.
(ii) If nucleic acid to be used is RNA, treat the whole assembly with diethyl pyrocarbonate treated (0.1%) water for 12-16 hours before autoclaving.
(iii) Keep the gel to be transferred ready.
(iv) Remove the lid of the device and keep aside.
(v) Remove retaining rim of the device by unscrewing nut and bolts.
(vi) Base plate is now exposed and is ready to accept the gel.
(vii) Bring the tray containing gel to be transferred on the top of base plate.
(viii) While holding the gel tray with both the hands, tilt the tray from the front and bring it very close (almost touching) to the base plate.
(ix) While holding the tray, give light push to the gel with the help of the thumb.
(x) Concomitantly, the gel tray should be pulled away from the gel.
(xi) After a few seconds, the gel from the gel tray will be transferred onto the base plate.

(xii) Place the retaining rim onto the base plate.
(xiii) Fasten the retaining rim with the help of nut and bolts.
(xiv) Ensure that clamp on the drain-out tube is tight enough to avoid leakage of any solution.
(xv) Pour the required solution.
(xvi) As per the need, whole of the assembly may be kept over a shaker.
(xvii) To remove the poured solution, the clamp on the drain-out pipe should be loosened.
(xviii) Once, the solution is drained out, fasten the clamp and pour the solution.
(xix) Perform such steps as per the protocol of your choice.
(xx) Cover and uncover the lid as and when required.
(xxi) Once the processing is over, remove lid.
(xxii) Remove nut bolts or any fastening mechanism.
(xxiii) Remove retaining rim.
(xxiv) Take the base plate containing the gel near to a blotter.
(xxv) Position the base plate onto the blotter where the gel has to be transferred.
(xxvi) While holding the base plate with both hands, tilt the base from the front and bring it very close (almost touching) to the place where the gel needs to be transferred.
(xxvii) While holding the base plate, give light push to the gel with the help of thumb. It is also possible to hold the base plate with one hand and use another hand to push the gel slowly for its transfer onto the blotting surface.
(xxviii) Concomitantly, the base plate should be pulled away from the gel.
(xxix) After a few seconds, the gel from the base plate stands transferred onto the blotting surface.
(xxx) If the purpose is not to transfer the gel onto the blotting surface but to photograph the gel, then perform the following sequence following step number (xx) onwards:
  (a) Bring the device near the photography unit
  (b) Uncover the lid
  (c) Remove the solution from the apparatus
  (d) During draining out of the solution, ensure that the gel is properly spread
  (e) Remove the retaining rim as in steps (xxii) and (xxiii) above
  (f) Since base plate is a transparent surface, the photography can easily be performed
(xxxi) During processing of the gel, the drain-out tube can easily be fitted tightly in the space between nut and bolt and the side walls of the retaining rim

THE MAIN ADVANTAGES OF THE PRESENT INVENTION ARE

The invention provides a gel processing and transfer device wherein both the features that is, the processing and the transfer capabilities are present in the same device that ensures intact gel during various processes that are involved after electrophoresis of nucleic acids and before placing the gel onto the membrane for the purpose of transfer of nucleic acid, and while transferring the gel from the device onto the membrane.

The claimed device has the following characteristics and uses:
  a. autoclavable at 121° C. under a pressure of 1.1 kg per square centimeters to ensure sterile environment to the gel.
  b. solutions can be drained out without tilting of the device.
  c. suitable for processing not only for agarose gel but also for other gels such as, but not limited to, polyacrylamide gels.
  d. suitable for staining the gels such as, but not limited to, staining proteins and nucleic acids using the recommended staining procedures.
  e. safe system for gel transportation from one place to another for the purpose such as, but not limited to, for taking permanent impressions of the gel for records.
  f. safe system for photography of the gel wherein after staining the gel, the gel need not to be tempered with for the purpose of clicking the photograph.
  g. transparent system for easy visibility.

What is claimed:

1. A gel processing and transfer device, useful for the processing and transferring of gels with minimal handling, said device comprising a base plate having a planar configuration for holding the gels; a retaining rim structure fastened to the base plate by a fastening means, and a lid to cover the retaining rim structure fastened to the base plate; wherein the retaining rim structure comprises of a plurality of side walls having a top and a bottom end; a horizontal plate located intermediate to the top and bottom ends of the side wall such that the side wall includes a protruded portion protruding beyond the horizontal plate, with a space defined between the horizontal plate and the base plate and outwardly of the protruded portion of the side wall and at least one "O" shaped ring being provided in the space to provide leak proof arrangement.

2. A device as claimed in claim 1, wherein the base plate is made up of materials selected from the group consisting of polycarbonate, acrylic, Plexiglas, glass, plastic, polyethylene, polypropylene, polyester, polymethacrylate, poly (1,4-cycohexylene dimethylene terephthalate) glycol and metals.

3. A device as claimed in claim 1, wherein the base plate has a thickness of at least 1 mm.

4. A device as claimed in claim 1, wherein the base plate has a drain-out device to decant the drained out solution.

5. A device as claimed in claim 4, wherein the drain-out has a hole cut in the base plate.

6. A device as claimed in claim 5, wherein the hole of the drain-out device has a nozzle.

7. A device as claimed in claim 6, wherein the nozzle on the drain-out device is made up of materials selected from the group consisting of polycarbonate, acrylic, Plexiglas, glass, plastic, polyethylene, polypropylene, polyester, polymethacrylate, poly (1,4-cycohexylene dimethylene terephthalate) glycol and metals.

8. A device as claimed in claim 6, wherein the nozzle on the drain-out device has a tubing attached thereto.

9. A device as claimed in claim 8, wherein the tube is made up of materials selected from the group consisting of rubber, latex rubber, silicone, platinum-cured silicone (for high purity and no peroxides), C-Flex (as opaque white thermoplastic elastomer formulated from styrene-ethylene-butadiene-styrene block co-polymer), low density polyethylene, fluorinated ethylene-propylene, Teflon polytetrafluoroethylene and silicone.

10. A device as claimed in claim 8, wherein the tube has an inner diameter that fits exactly to an open end of the nozzle and is fixed with a clamp to control the flow of the solution.

11. A device as claimed in claim 1, wherein the side walls are made of materials selected from the group consisting of polycarbonate, acrylic, Plexiglas, glass, plastic, polyethylene, polypropylene, polyester, polymethacrylate, poly (1,4-cycohexylene dimethylene terephthalate) glycol and metals.

12. A device as claimed in claim 1, wherein the side wall has a thickness of at least 1 mm.

13. A device as claimed in claim 1, wherein the side wall has a height of at least 1 cm.

14. A device as claimed in claim 1, wherein the fastening means comprise nuts and bolts.

15. A device as claimed in claim 14, wherein the fastening means are made of materials selected from the group consisting of polycarbonate, acrylic, Plexiglas, glass, plastic, polyethylene, polypropylene, polyester, polymethacrylate, poly (1,4-cycohexylene dimethylene terephthalate) glycol and metals.

16. A device as claimed in claim 1, wherein the "O" shaped ring is made of materials selected from the group consisting of rubber, latex rubber, silicone, platinum-cured silicone (for high purity and no peroxides), C-Flex (as opaque white thermoplastic elastomer formulated from styrene-ethylene-butadiene-styrene block co-polymer), low density polyethylene, fluorinated ethylene-propylene, Teflon polytetrafluoroethylene and silicone.

17. A device as claimed in claim 1, wherein the "O" shaped ring is fitted around the protruded portion of the side wall of the retaining rim.

18. A device as claimed in claim 1, wherein the lid is made of materials selected from the group consisting of polycarbonate, acrylic, Plexiglas, glass, plastic, polyethylene, polypropylene, polyester, polymethacrylate, poly (1,4-cycohexylene dimethylene terephthalate) glycol and metals.

19. A device as claimed in claim 1, wherein the lid has a thickness of at least 1 mm.

20. A device as claimed in claim 1, wherein the lid rests on the top of end of the side wall of the retaining rim.

21. A device as claimed in claim 1, wherein the lid has at least four protrusions that keep the lid fixed onto the side wall of the retaining rim from outside.

22. A device as claimed in claim 21, wherein the protrusions of the lid are made from material selected from the group consisting of polycarbonate, acrylic, Plexiglas, glass, plastic, polyethylene, polypropylene, polyester, polymethacrylate, poly (1,4-cycohexylene dimethylene terephthalate) glycol and metals.

23. A device as claimed in claim 21, wherein the protrusions on the lid have a thickness of at least 1 mm.

24. A device as claimed in claim 1, wherein the retaining rim and the lid are molded.

25. A device as claimed in claim 1, wherein the device is constructed with autoclave material.

26. A device as claimed in claim 1, wherein the device is constructed with metal with no heat-sensitive component.

27. A device as claimed in claim 1, wherein the device is transparent to light.

28. A device as claimed in claim 1, further comprising: a rubber strip in the space and between the horizontal base plate with the at least one "O" shaped ring located intermediate the rubber strip and the protruded portion.

* * * * *